Figure 1:
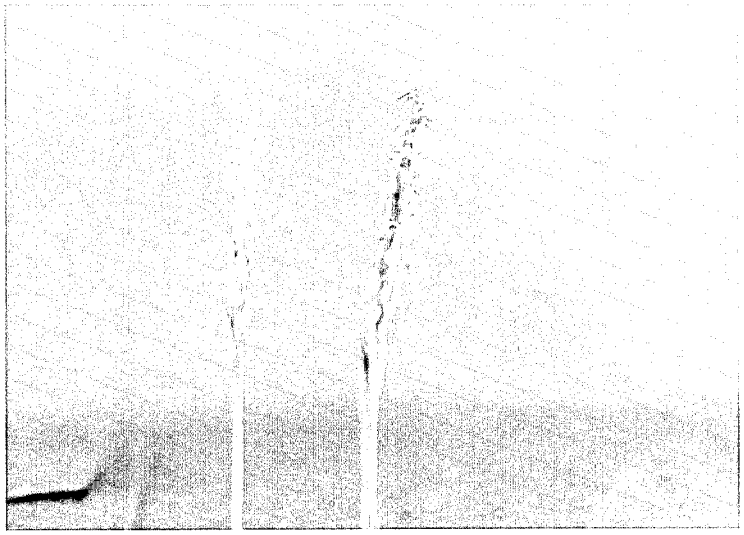

United States Patent [19]

Whiting

[11] Patent Number: Plant 7,074

[45] Date of Patent: Dec. 12, 1989

[54] ZOYSIA JAPONICA GRASS PLANT ZT-11

[76] Inventor: Hubert F. Whiting, 7636 Madera Ave., Hesperia, Calif. 92345

[21] Appl. No.: 282,461

[22] Filed: Dec. 9, 1988

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

I disclose that my herein invention of a new variety of Zoysia grass plant, was discovered by me through my cross-pollination of selected varieties of Zoysia grass plants, then through asexual repropagation, selected the new and distinct variety of Zoysia grass plant ZT-11, which produces an outstanding dark olive green color with a uniform turfgrass surface that has virtually no seedheads with a very upright growth characteristic from stolons and rhizomes, then held complete green color throughout several winter periods. The anthers of the new claimed variety of Zoysia grass plant are dark purplish red color as defined by the ISCC-NBS centroid color chart; the stigmas are pale yellow green color, as defined by the ISCC-NBS centroid color chart; the stolons are a very dark red color, as defined by the ISCC-NBS centroid color chart with stolon internodes closer together. The entire plant of the new claimed variety of Zoysia grass plant ZT-11, is glabrous except on the inside of the color just above the ligule where several long hairs are present. The electrophoresis isoenzyme banding patterns show distinct uniqueness of the new claimed variety of Zoysia grass plant designated ZT-11.

3 Drawing Sheets

The present invention and discovery relates to a new and distinct variety of Zoysia grass plant, which was developed by me through a series of cross-pollination of collected varieties of Zoysia grass plants of Zoysia Japonica, a variety named "El Toro" and a Zoysia Japonica ZT-167 a hybrid variety that I developed. This cross-pollination was done by me at Fallbrook, Calif., U.S.A. about 34 degrees north latitude. I harvested seeds from this cross-pollination of selected varieties of Zoysia grass plants and planted these seeds out in germinating trays. About six weeks after the seeds germinated, I selected the one hundred most rapidly establishing plants. I then transplanted each separate seedling into one gallon containers. As these seedlings grew and developed, I once again selected the most aggressively establishing and most desirable for turfgrass potential; this left forty five seedling, these forty five seedlings were then each individually broken up by me into small pieces of stolons. I then planted these small pieces of stolons into the soil in an area that was three feet square. When this process was completed, I had forty five individual seedlings planted in forty five three foot square plots, all asexually planted by me. The location of this transplanting was at Fallbrook, Calif., U.S.A. Once these forty five three foot square plots became established through the spreading of the planted stolons. I formed a turfgrass surface through regular mowing. I again made selections from the forty five plots. The selections I made this time were again individually transplanted by me asexually, by breaking sufficient stolon material of each separate selection to further replant the now ten selections into larger individual separate plots of ten feet by eight. Once these larger plots became established through the spreading of the planted stolons. I formed a turfgrass surface through regular mowing. I again made selections from these ten plots. The new claimed variety of Zoysia grass plant, is one of those selections, and which I have designated ZT-11. This new selected variety of Zoysia grass plant spreads by stolons and rhizomes to produce an excellent turfgrass surface when mown regularly. I observed that this new claimed variety produced an outstanding deep rich green color and a very uniform turfgrass surface with virtually no seedheads also, held complete green color throughout several replicated randomized trial winter periods, when compared to the closest known variety of Zoysia grass plant identified as ZT-4, which is my U.S.A. Plant patent application Ser. No. 07/026,140 filing date 03/16/87. The new claimed variety of Zoysia grass plant has a superior rich green color and produces very few seedheads that results in a very uniform turfgrass surface, the upright growth characteristic of the new claimed variety enables mowing with a rotary mower without scalping, whereas the closest known variety ZT-4 does scalp, also this upright growth characteristic produces less thatch build-up. During the continued asexual reproduction by stolons, I have confirmed that the above-described characteristics are transmitted through succeeding propagations, and have confirmed that the new claimed variety of Zoysia grass plant has the following unique combination of characteristics. The new and distinct variety of Zoysia grass plant is illustrated in the accompanying color photographs, with the photographs of the closest known variety of Zoysia grass plant known as ZT-4. The most noticeable variations between the new claimed variety of Zoysia grass plant and the closest known variety of Zoysia grass plant ZT-4, is that the new claimed variety of Zoysia grass plant is an outstanding dark olive green color with a more upright growth characteristic and the stolon is a very dark red color with internodes closer together; the new claimed variety is glabrous except on the inside of the collar, just above the ligule where several long hairs are present; the new claimed variety has stigmas and anthers of different color, before dehiscence, when compared to the closest known variety of Zoysia grass plant ZT-4; the new claimed variety has unique isoenzyme electrophoresis banding patterns, when compared to the closest known variety of Zoysia grass plant known as ZT-4.

IN THE DRAWING:

FIG. 1. is a photograph of two spikes taken from the same test area, the spike on the right in the photograph is of the new claimed variety of Zoysia grass plant ZT-11, with the spike on the left in the photograph is of the closest known variety of Zoysia grass plant ZT-4; this photograph shows the pale yellow colored anthers, color number 89.p.y. with stigmas of yellowish white color, color number 92.y white as defined by the ISCC-NBS centroid color chart, of the closest known variety of Zoysia grass plant ZT-4, when compared to the dark purplish red colored anthers color number 259.d.pr with stigmas of pale yellow green color, color number 121.p.yg as defined by the ISCC-NBS centroid color chart of the new claimed Zoysia grass plant ZT-11.

Figure 2:
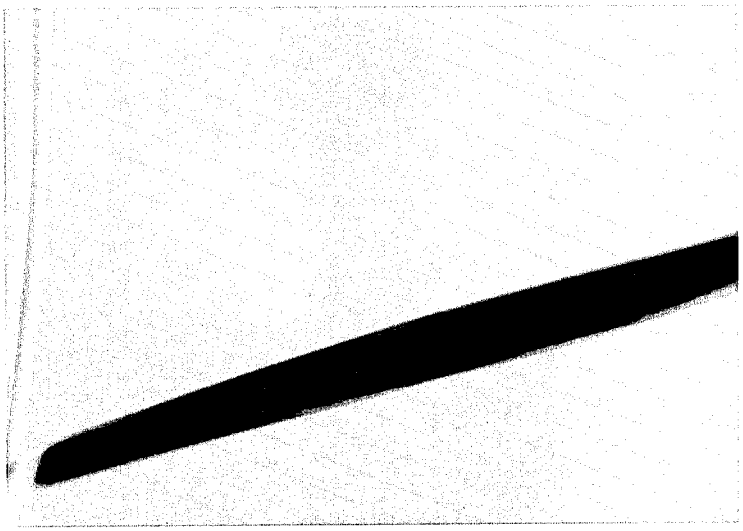

FIG. 2. is a photograph of a leaf on the new claimed variety of Zoysia grass plant ZT-11 taken from the same test area; this photograph shows the glabrous leaf.

Figure 3:
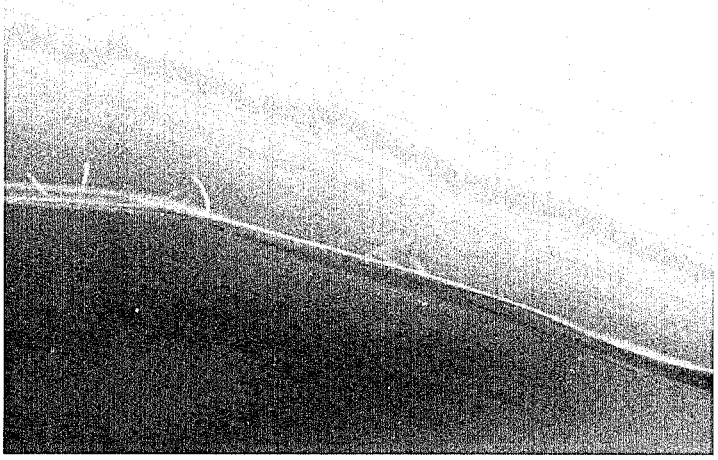

FIG. 3. is a photograph of a leaf of the closest known variety of Zoysia grass plant ZT-4 taken from the same test area; this photograph shows the sparsely pubescent upper leaf area.

Figure 4:
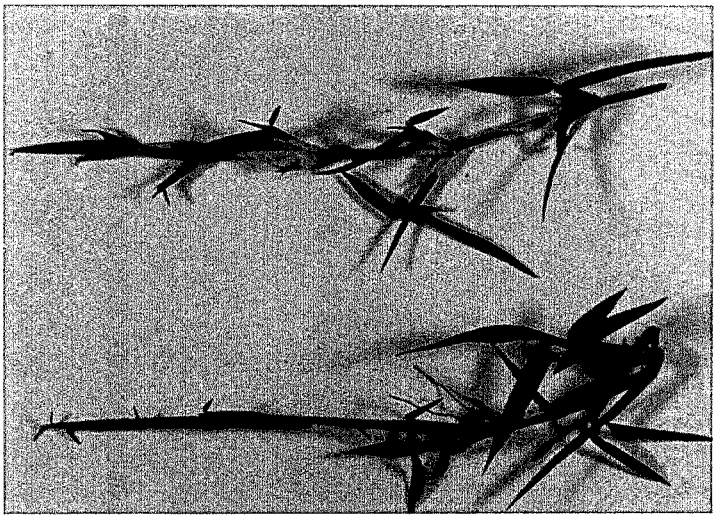

FIG. 4. is a photograph of two stolons taken from the same test area; this photograph shows the stolon on the top in the photograph of the new claimed variety of Zoysia grass plant ZT-b 11 with internodes closer together and the color of the stolon very dark red color, color number 17.v.d red as defined by the ISCC-NBS centroid color chart also the color of the leaf color number 126.d.OL G as defined by the ISCC-NBS centroid color chart, when compared to the stolon on the bottom in the photograph which is the closest known variety of Zoysia grass plant ZT-4, which has stolon internodes farther apart and that has yellow green colored stolons also the leaf shows the deep yellow green color number 118.deep YG as defined by the ISCC-NBS centroid color chart.

Figure 5:
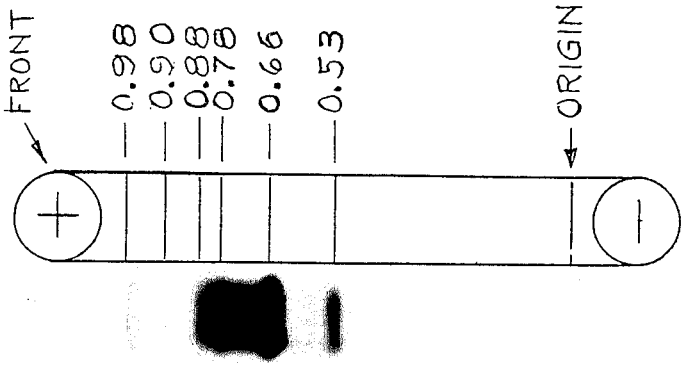

FIG. 5. This photograph shows the electrophoresis zymogram patterns of the esterase (EST) isoenzyme banding pattern, of the new claimed variety of Zoysia grass plant ZT-11.

Figure 6:
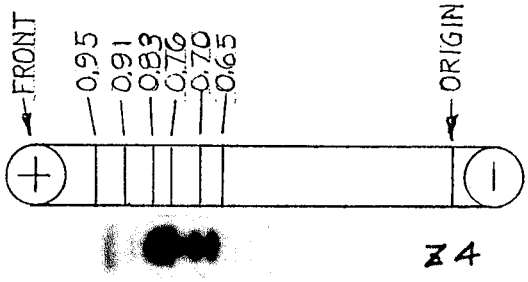

FIG. 6. This photograph shows the electrophoresis zymogram patterns of the esterase (EST) isoenzyme banding pattern, of the closest known variety of Zoysia grass plant ZT-4. Both photographs FIG. 5. and FIG. 6. were taken from the same test area.

A detailed description of the new and distinct variety of Zoysia grass plant ZT-11 is:

(a) A beautiful dark olive green color, color number 126.d.OL G, of the ISCC-NBS centroid color chart.
(b) The grass is low-growing, with an upright erect growth characteristic.
(c) The grass spreads by stolons and rhizomes, forming a dense upright, uniform surface, with an extensive root system; stolons are a very dark red color, color number 17.v.d.Red of the ISCC-NBS centroid color chart with internodes 2–2.5 centimeters apart.
(d) Culms vary in height from 16–25 centimeters.
(e) Leaves rolled in bud shoot.
(f) The leaf blade is flat, and gradually tapering to an acute point.
(g) The first mature leaf is 2–3 millimeters in width and 10–16 centimeters long.
(h) The leaf blade is glabrous.
(i) The ligule is a very small ciliate fringe 0.25 millimeters in height, with several long hairs just above the ligule on the inside of the collar 1–3 millimeters long.
(j) Auricles are absent.
(k) The collar is broad, and continuous.
(l) The sheath is glabrous, except on the inside of the collar just above the ligule, where several long hairs are present.
(m) The entire plant is glabrous, except on the inside of the collar just above the ligule, where several long hairs are present.
(n) The inflorescence consists of a single spike at the top of the main stem.
(o) The spike contains stigmas of pale yellow green color, color number 121 p.YG of the ISCC-NBS centroid color chart; the anthers are dark purplish red color, color numnber 259.d.pr of the ISCC-NBS centroid color chart; the glumes are 2–3 millimeters long, blunt at their base, pointed at their tips.

A detailed description of the closest known variety of the species of Zoysia grass plant ZT-4 is:

(a) An attractive deep yellow green color, color number 118.deep YG of the ISCC-NBS centroid color chart.
(b) The grass is low-growing, erect in habit.
(c) The grass spreads by stolons and rhizomes, forming a dense, uniform surface, with an extensive root system; stolons 1 millimeter in width with internodes 2.5–3 centimeters apart.
(d) Culms vary in height from 18–22 centimeters.
(e) Leaves rolled in bud shoot.
(f) The leaf blade is flat, and gradually tapering to an acute point.
(g) The first mature leaf is 3–4 millimeters in width and 8–12 centimeters long.
(h) The upper leaf surface is sparsely pubescent.
(i) The ligule is a very small ciliate fringe 0.25 millimeters in height, with several long hairs just above the ligule on the inside of the collar 1–2 millimeters long.
(j) Auricles are absent.
(k) The collar is broad, and continuous.
(l) The sheath is glabrous, and split with separate margins.
(m) The entire plant is glabrous, except on the upper leaf surface and on the inside of the collar just above the ligule where several long hairs are present.
(n) The inflorescence consists of a single spike at the top of the main stem.
(o) The spike contains stigmas of yellowish white color, color number 92.y white of the ISCC-NBS centroid color chart; the anthers are pale yellow color, color number 89.p.Y of the ISCC-NBS centroid color chart; the glumes are 2–3 millimeters long, blunt at their base, pointed at their tips.

I claim:

1. A new and distinct variety of grass plant, Zoysia ZT-11 as herein described and illustrated.

* * * * *

Z4